US00PP29343P2

(12) United States Plant Patent
Hansen

(10) Patent No.: US PP29,343 P2
(45) Date of Patent: May 29, 2018

(54) ***MANFREDA* PLANT NAMED 'MINT CHOCOLATE CHIP'**

(50) Latin Name: ***Manfreda undulata* (Klotzsch) Rose**
Varietal Denomination: Mint Chocolate Chip

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days. days.

(21) Appl. No.: 15/530,440

(22) Filed: Jan. 13, 2017

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373, 372
CPC ..... A01H 5/12
See application file for complete search history.

*Primary Examiner* — Kent L Bell

(57) ABSTRACT

A new and unique *Manfreda* plant named 'Mint Chocolate Chip' characterized by long arching foliage with silvery-blue-green foliage having irregular greyed-purple spotting. The flowers of burgundy tepals, filaments and styles generate large volumes of nectar and are highly attractive to hummingbirds.

1 Drawing Sheet

Botanical classification: *Manfreda undulata* (Klotzsch) Rose.

Variety denomination: 'Mint Chocolate Chip'.

BACKGROUND OF THE INVENTION

The present invention relates to the new and distinct *Manfreda* plant, *Manfreda* 'Mint Chocolate Chip' hybridized by the inventor at a wholesale perennial nursery in Zeeland, Mich., USA as a result of a selfing of *Manfreda* 'Chocolate Chips' (not patented). The individual seedling was one selected from a cross on Apr. 15, 2011 that batch originally sown on Aug. 1, 2011. Through trials at the same nursery the plant was originally assigned the breeder code Manf-11-06-20. The new plant has been successfully asexually propagated initially by division at the same nursery in Zeeland, Mich. and also by sterile shoot-tip tissue culture. Both methods of asexual propagation systems have been found to produce stable and identical plants that maintain all the unique characteristics of the original plant.

No plants of *Manfreda* 'Mint Chocolate Chip' have been sold, under this or any name, in this country or anywhere in the world, prior to the filing of this application, nor has any disclosure of the new plant been made prior to the filing of this application with the exception of that which was disclosed or sold within one year of the filing of this application, and was either derived directly or indirectly from the inventor.

BRIEF SUMMARY OF THE INVENTION

*Manfreda* 'Mint Chocolate Chip' differs from its parent as well as all other *Manfreda, Agave* and ×*Mangave* known to the applicant. The most similar known *Manfreda* cultivar is 'Chocolate Chips' (not patented). Compared with 'Chocolate Chips' the new plant has wider and more silvery foliage. Compared with ×*Mangave* 'Moonglow' U.S. Plant patent application Ser. No. 15/330,178 the new plant has smaller spotting, broader and more undulated foliage. Compared with ×*Mangave* 'Bloodspot' (not patented) the new plant is larger in habit, has larger spotting on broader and longer leaves with more undulation. Compared with ×*Mangave* 'Jaguar' the new plant has more undulated foliage with larger burgundy spotting. Compared with ×*Mangave* 'Macho Mocha' the new plant has thinner, less broad foliage, and the spotting is larger and less dense.

The new plant, 'Mint Chocolate Chip', is unique from all of these *Agave,* ×*Mangave* and *Manfreda* known to the inventor by the following combined traits:

1. Long, horizontal to arching, silvery-blue-green foliage.
2. Foliage develops irregular greyed-purple spotting throughout upper and lower surfaces when plant is grown with exposure to ultraviolet light;
3. Moderate to rapid growth rate with good natural pup production;
4. Burgundy flowers with long filaments and style on stiff, tall scapes.

BRIEF DESCRIPTION OF THE DRAWINGS

The photographs of the new plant demonstrate the overall appearance of the new plant including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
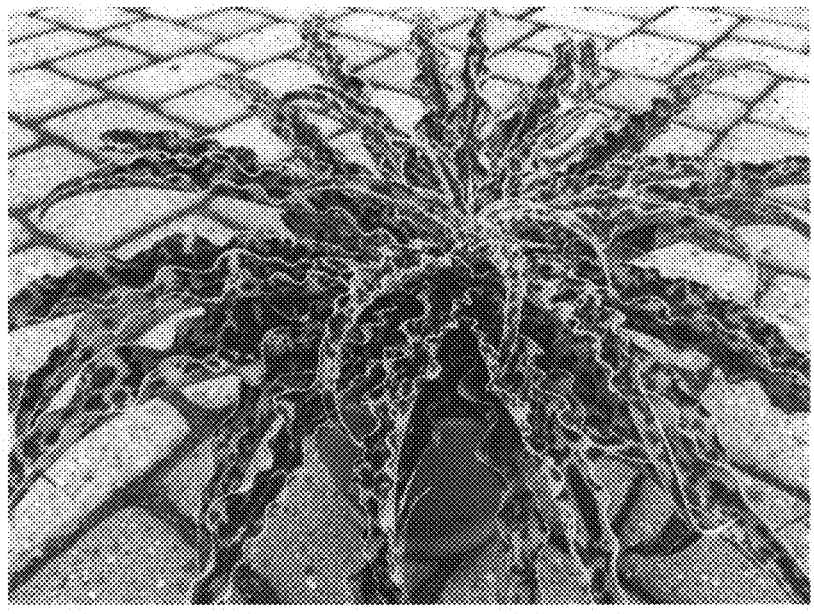
FIG. 1 shows a one-year-old plant having been grown in a container outdoors in Raleigh, N.C.
Figure 2:
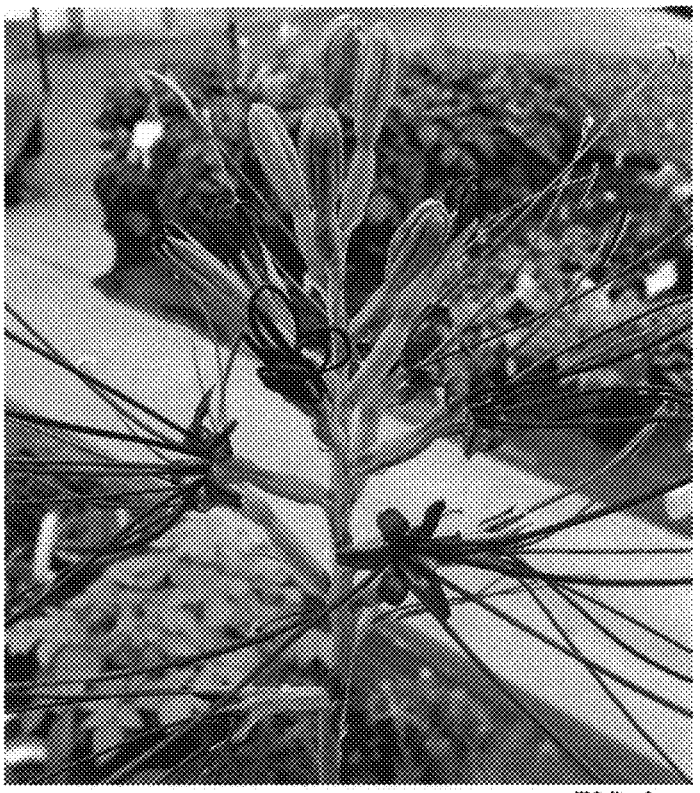
FIG. 2 shows a close-up of the flower of four-year-old new plant in flowering in a greenhouse in Zeeland, Mich.

The following descriptions and color references are based on the 2001 edition of The Royal Horticultural Society Colour Chart except where common dictionary terms are used. The new plant, *Manfreda* 'Mint Chocolate Chip', has not been observed under all possible environments. The phenotype may vary slightly with different environmental conditions, such as temperature, light, fertility, moisture and maturity levels, but without any change in the genotype. The following observations and size descriptions are of a two-year old plant in a commercial wholesale greenhouse in Zeeland, Mich. with supplemental water and fertilizer as needed.

Botanical classification: *Manfreda undulata.*

Variety denomination: 'Mint Chocolate Chip'.

Parentage: *Manfreda* 'Chocolate Chips' as female (seed) parent and 'Chocolate Chips' as male (pollen) parent.

Propagation: Division and sterile shoot-tip tissue culture.

Time to initiate roots from tissue culture: About 21 days.

Growth rate: Moderate to rapid.

Crop time: About 10 to 14 weeks to finish during lengthening spring days from an established 25 mm tissue culture plug to a 65 mm diameter container.

Rooting habit: Fleshy, lightly branching, with roots up to 15 cm long.

Root color: Nearest RHS 158C.

Plant shape and habit: Succulent herbaceous perennial with basal rosettes of about 50 leaves radially emerging and arching from central rhizome extending below the base of the plant when grown in containers, producing a radially-symmetrical, round mound.

Plant size: Foliage height about 22.0 cm tall from soil line to the top of the leaves and about 60.0 cm wide at the widest point slightly below base.

Foliage description: Gladiate; simple; margins finely dentate with flexible teeth, teeth about 1.0 mm long and spaced about 2.0 mm apart; apex narrowly acute; base truncate, sessile, clasping.

Number of leaves: About 50 per plant.

Leaf blades: Finely dentate; to about 39.0 cm long, about 5.0 cm wide at base and 1.5 mm thick, average about 35.0 cm long, 3.8 cm wide and 4.0 mm thick; typically conduplicate toward base slightly flattening distally, with coarse undulation about 1.0 cm deep and bi-laterally symmetrical; glabrous and glaucous adaxial and abaxial; with dark burgundy spots to about 2.0 cm long and 0.5 cm across.

Foliage fragrance: None observed.

Leaf blade color:

*Adaxial* (*young*).—Nearest RHS N138B with spots intensifying with ultraviolet light exposure to nearest RHS 187A; Abaxial (young): Between RHS 138A and RHS 13BB with spots intensifying with ultraviolet light exposure to between RHS 187B and RHS 187A.

*Adaxial* (*mature*).—Between RHS 137C and RHS N138B with spots intensifying with ultraviolet light exposure between RHS 139A and RHS N187A and a light glaucous overtone of nearest a blend between RHS 190A and RHS 191C; Abaxial (mature): between RHS 137C and RHS 138A with spots of nearest RHS 139A; and a light glaucous overtone of nearest a blend between RHS 190A and RHS 191C.

*Teeth*.—Nearest RHS 158D.

Petiole: Sessile.

Veins: Parallel; not distinct abaxial or adaxial.

Peduncle: Terete; glaucous; glabrous; stiff; strong; with cauline leaves nearly adpressed along surface; about 160 cm long and 1.5 cm diameter at base; attitude upwards, erect.

Peduncle color: With at base between RHS N187A and RHS N187B, distally between RHS N187C and RHS N187D with undertones of nearest RHS N138C.

Pedicel: Terete; glaucous; glabrous; stiff; strong; about 6.0 mm long and 2.5 mm diameter; attitude mostly upright.

Pedicel color: Nearest RHS 138B.

Cauline leaves: About 18 per scape; gladiate to lanceolate; simple, fleshy, glabrous; margins finely dentate with flexible teeth; narrowly apex acute; base truncate, sessile, clasping; proximally about 20.0 cm long and about 1.2 cm wide at base, decreasing distally; color adaxial and abaxial same as basal leaves.

Buds one day prior to opening: Elongated globose; terminal bulb about 2.8 cm long and about 1.0 cm across; proximal tube about 2.5 cm long and 6.0 mm across; overall about 5.2 cm long.

Bud color: Nearest RHS 138A.

Flower description: Perfect, actinomorphic; from flower base to tip of anthers about 15.0 cm long and opening to about 13.0 cm across; lasting about 3 to 4 days per flower; flowering period about three weeks in late winter in Michigan greenhouse; producing abundant nectar; approximately 36 flowers per scape; attitude mostly upright.

Flower fragrance: Very faint to none.

Tepals: Six in two sets of three; glaucous abaxial; glabrous both adaxial and abaxial; acute apex and fused in basal 11.0 mm; outer set recurved about 3.2 cm long, about 6.0 mm wide above fusion point; inner set about 3.2 cm long and 6.0 mm wide at base.

Tepal color: Adaxial nearest RHS 187A, abaxial between RHS 138C and RHS N138B with undertone of nearest RHS N187 and pronounced midrib of nearest RHS 138B.

Androecium: Six.

*Filaments*.—Six; stiff, straight, divaricate; about 12.0 cm long and 2.0 mm diameter at base; color between RHS 187C and RHS 187B.

*Anther*.—Dorsifixed; longitudinal; about 16.0 mm long and 1.5 mm diameter before opening; after dehiscence curving backward; color between RHS 177A and RHS 178A.

*Pollen*.—Abundant; color nearest RHS 18A.

Gynoecium: Single.

*Style*.—Extending to 9.8 cm long and 2.0 mm diameter at base; color between RHS 177A and RHS 178A.

*Stigma*.—Globose, apex tri-lobed; about 2.5 mm tall and 3.0 mm across top; color side nearest RHS N186B; top stigmatic surface in tri-pointed star, color nearest RHS N187A.

*Ovary*.—Inferior.

Fruit: Dehiscent, tri-valved, loculicidal capsule; apex abruptly acute; base slightly tapered; about 3.8 cm long and 1.8 cm across.

Fruit color: When immature nearest RHS N138A; at dehiscence RHS N199A along veins and RHS 201C in furrowed depressions between septa nearest RHS 199D in remainder of capsule.

Seed: Flattened, near round to semi-circular; about 100 to 200 per capsule; about 5.0 to 6.0 mm across and about 1.0 mm thick; color nearest RHS 202A.

Disease resistance: *Manfreda* 'Mint Chocolate Chip' has not been observed to be resistant to diseases beyond that which is normal for ×*Mangave, Agave* or *Manfreda*. The plant is xeromorphic and survives well with minimal water once established. The new plant is hardy at least from USDA zone 7b to 10. Full extent of winter hardiness has not been tested.

It is claimed:

1. A new and distinct cultivar of ornamental *Manfreda* plant named 'Mint Chocolate Chip' as herein described and illustrated, suitable for the garden or as a potted plant in the garden or home.

* * * * *